(12) United States Patent
Kouno et al.

(10) Patent No.: US 6,265,577 B1
(45) Date of Patent: Jul. 24, 2001

(54) PYRAZOLOPYRIDYLPYRIDAZINONE DERIVATIVES AND PROCESS FOR THE PREPARATION THEREOF

(75) Inventors: Yasushi Kouno, Oyama; Takenobu Ogata, Tokyo; Katsuya Awano, Oyama; Kayoko Matsuzawa, Ageo; Taroh Tooru, Nogi-machi, all of (JP)

(73) Assignee: Kyorin Pharmaceuticals Co., Ltd., Tokyo (JP)

( * ) Notice: Subject to any disclaimer, the term of this patent is extended or adjusted under 35 U.S.C. 154(b) by 0 days.

(21) Appl. No.: 09/269,734
(22) PCT Filed: Sep. 26, 1997
(86) PCT No.: PCT/JP97/03434
  § 371 Date: Apr. 5, 1999
  § 102(e) Date: Apr. 5, 1999
(87) PCT Pub. No.: WO98/14448
  PCT Pub. Date: Apr. 9, 1998

(30) Foreign Application Priority Data

Oct. 4, 1996 (JP) .................................................. 8-283148

(51) Int. Cl.$^7$ ..................... C07D 237/02; A61K 31/4965
(52) U.S. Cl. ....................................... 544/239; 514/252.06
(58) Field of Search ......................... 544/239; 514/252.06

(56) References Cited

FOREIGN PATENT DOCUMENTS

02243689 * 9/1990 (JP) .

* cited by examiner

*Primary Examiner*—Mukund J. Shah
*Assistant Examiner*—Sudhaker B. Patel
(74) *Attorney, Agent, or Firm*—Oblon, Spivak, McClelland, Maier & Neustadt, P.C.

(57) ABSTRACT

Novel pyrazolopyridylpyridazinone derivatives characterized by being represented by general formula (1) and pharnacologically acceptable salts thereof, which exhibit a phosphodiesterase inhibiting activity and have a selective potent bronchodilating effect on the respiratory tract; a process for the preparation of them; and bronchodilators containing the same as the active ingredient; wherein $R^1$ is $C_1$–$C_4$ lower alkyl or $C_3$–$C_6$ cycloalkyl; and $R^2$, $R^3$, $R^4$ and $R^5$ are each independently hydrogen, $C_1$–$C_4$ lower alkyl or phenyl, or alternatively $R^3$ and $R^5$ may be united to form a double bond.

8 Claims, No Drawings

PYRAZOLOPYRIDYLPYRIDAZINONE DERIVATIVES AND PROCESS FOR THE PREPARATION THEREOF

TECHNICAL FIELD

The present invention relates to novel pyrazolopyridinepyridazinone derivatives with phosphodiesterase-inhibiting activity and with selective-to-respiratory tract and potent bronchodilating effect and process for preparing the same.

BACKGROUND TECHNOLOGIES

Compounds with dihydropyridazinone and pyridazinone groups substituted at 3-position of pyrazolopyridine ring have been disclosed in Japanese Unexamined Patent publication Nos. Hei 2-243689 and Hei 4-253978. However, with the compounds claimed in these unexamined patent publications, substituents at 2-position of pyrazolopyridine ring are limited to aryl groups such as benzene derivatives, including no inventive compounds wherein they are alkyl groups. Also, pyrazolopyridine derivatives with bronchodilating effect are disclosed in Japanese Unexamined Patent Publication No. Hei 8-12673, but compounds disclosed therein have quite different structure from that of the inventive compounds.

Since it was discovered that the bronchodilating effect is caused through enhanced cyclic AMP and GMP in cells, enzymes that decompose cyclic AMP and GMP and inhibiting drugs of phosphodiesterase are attracting an attention as bronchodilator. While theophylline is mentioned for a common drug as an inhibiting drug of phosphodiesterase, theophylline has low selectivity to target organ. For this reason, when using theophylline to asthmatic patients for the purpose of bronchodilating effect, undesirable effects such as increased heart rate, vomition and central action occur very frequently as well. Developing a drug that acts selectively to respiratory tract being a target organ and expresses the bronchodilating effect via potent phosphodiesterase-inhibiting activity is being desired strongly as an ideal drug with low side effect.

As a result of diligent studies an a compound with phosphodiesterase-inhibiting activity and with selective-to-respiratory tract and potent bronchodilating effect, the inventors have found that novel pyrazolopyridinepyridazinone derivatives with different structure from that of bronchodilators known so far have high safety, too, and have selective-to-respiratory tract and potent bronchodilating effect, leading to the completion of the invention.

Namely, the invention provides pyrazolopyridinepyridazinone derivatives characterized by being represented by a general formula (1)

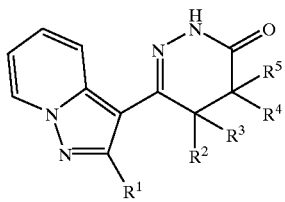

(1)

[wherein $R^1$ denotes a lower alkyl group with carbon atoms of 1 to 4 or cycloalkyl group with carbon atoms of 3 to 6, and $R^2$, $R^3$, $R^4$ and $R^5$ denote identically or differently hydrogen atoms, lower alkyl groups with carbon atoms of 1 to 4 or phenyl groups, or $R^3$ and $R^5$ may combine to form a double bond], pharmacologically acceptable salts, and bronchodilator having at least one or more kinds of them as effective ingredients.

For the pharmacologically acceptable salts of the compounds represented by the general formula (1) in the invention, acid adducts like hydrochloride, hydrobromide, citrate, methanesulfonate and tartrate are mentioned.

Moreover, in the general formula (1) of the invention, "lower alkyl group" indicates straight chain or branched hydrocarbons with carbon atoms of 1 to 4 such as methyl, ethyl and propyl and, for "cycloalkyl group", cyclic hydrocarbons with carbon atoms of 3 to 6 are mentioned. Moreover, for "halogen atom", chlorine, bromine and iodine atoms are mentioned.

According to the invention, compounds with $R^3$ and $R^5$ not forming a double bond among compounds represented by the general formula (1) aforementioned, i.e. compounds represented by a general formula (1a)

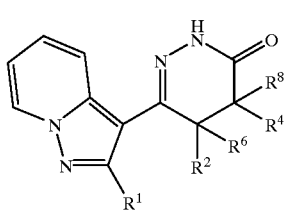

(1a)

[wherein $R^1$ is as described above, and $R^2$, $R^4$, $R^6$ and $R^8$ denote identically or differently hydrogen atoms, lower alkyl groups with carbon atoms of 1 to 4 or phenyl groups], can be prepared by reacting compounds represented by a following general formula (6) with hydrazine.

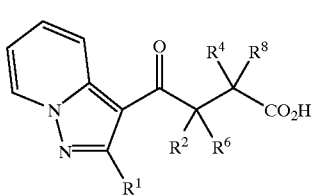

(6)

[wherein $R^1$, $R^2$, $R^4$, $R^6$ and $R^8$ are as described above].

The reaction can be conducted at room temperature to solvent-refluxing temperature as a reaction temperature in an organic solvent, for example, benzene, toluene, acetic acid, ethanol or the like. At this time, ethanol is preferable as a reaction solvent and the reaction temperature is preferable to be refluxing temperature under heat.

Moreover, compounds with $R^3$ and $R^5$ combined to form a double bond in the general formula (1), i.e. compounds represented by a general formula (1c)

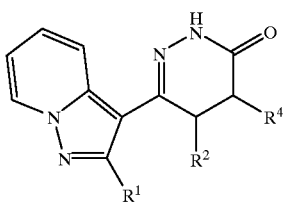
(1c)

[wherein $R^1$, $R^2$ and $R^4$ are as described above], can be prepared by oxidizing compounds represented by a general formula (1b)

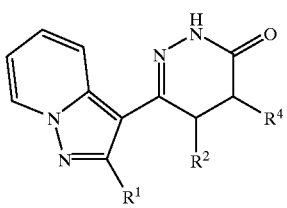
(1b)

[wherein $R^1$, $R^2$ and $R^4$ are as described above].

It is preferable to conduct the reaction by reacting with bromine in a solvent of acetic acid, and the reaction temperature is preferable to be 50 to 60° C.

The compounds represented by the general formula (6) aforementioned can be prepared through following three routes.

Synthetic route 1

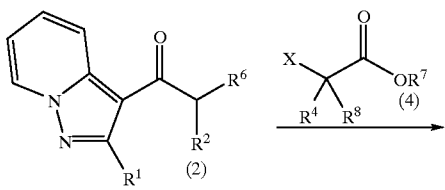

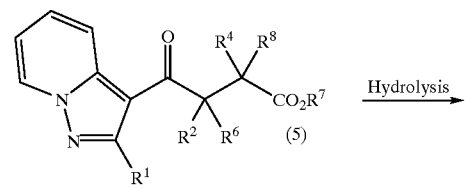

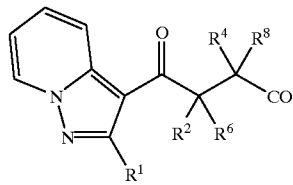

Synthetic route 2

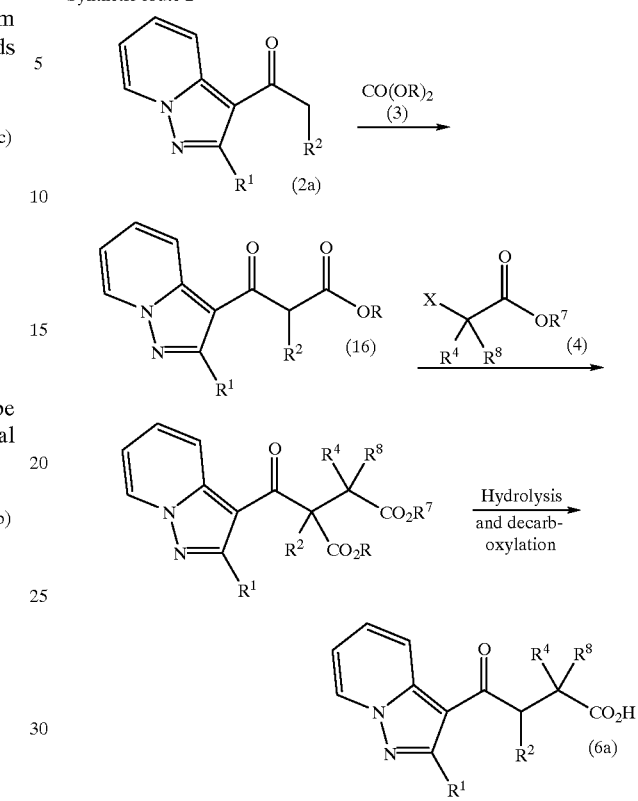

Synthetic route 3

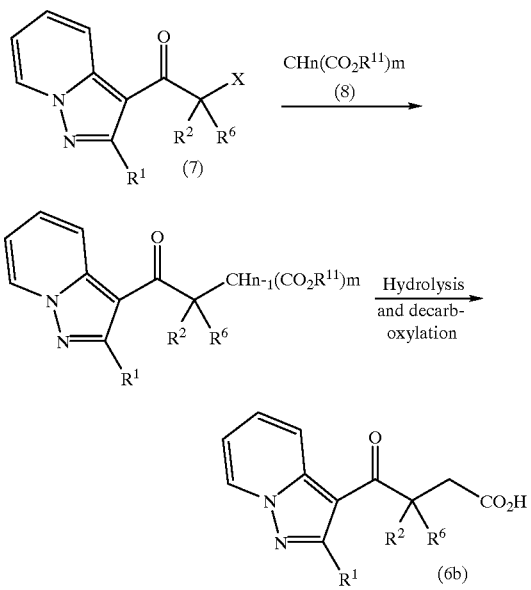

In the synthetic route 1, compounds represented by a general formula (5)

(5)

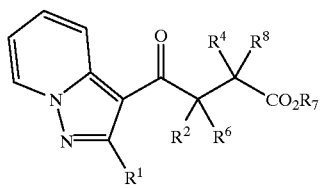

[wherein $R^1$, $R^2$, $R^4$, $R^6$ and $R^8$ are as described above, and $R^7$ denotes a lower alkyl group with carbon atoms of 1 to 3], can be prepared by reacting compounds represented by a general formula (2) with compounds represented by a general formula (4)

(2)

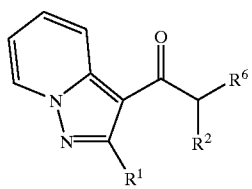

[wherein $R^1$, $R^2$ and $R^6$ are as described above].

(4)

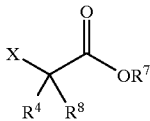

[wherein X denotes a halogen atom, and $R^4$, $R^7$ and $R^8$ are as describe above].

It is preferable to conduct the reaction at 0° C. to solvent-refluxing temperature, though the reaction temperature is not restricted particularly, in the presence of inorganic base such as potassium t-butoxide or potassium hydride, preferably sodium hydride, using tetrahydrofuran, 1,4-dioxane, or 1,2-dimethoxyethane, preferably dimethylformamide.

In the synthetic route 1, the compounds of general formula (6)

(6)

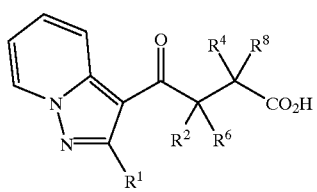

[wherein $R^1$, $R^2$, $R^4$, $R^6$ and $R^8$ are as described above], can be prepared by hydrolyzing the compounds represented by the general formula (5) aforementioned.

In the case of acid catalyst, it is preferable to conduct the hydrolysis by heating to 80 to 120° C., using hydrochloric acid or hydrobromic acid. Moreover, in the case of alkali catalyst, it is preferable to conduct at room temperature in an alcoholic solvent such as methanol or ethanol or in a solvent such as tetrahydrofuran or dimethylformamide, using aqueous solution of sodium hydroxide or aqueous solution of potassium hydroxide.

In the synthetic route 2, compounds represented by a general formula (16)

(16)

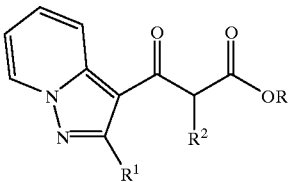

[wherein $R^1$ and $R^2$ are as described above, and R denotes a lower alkyl group with carbon atoms of 1 to 3], can be prepared by reacting compounds represented by a following general formula (2a) with compounds represented by a general formula (3)

(2a)

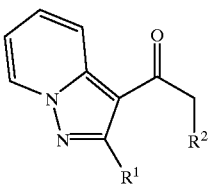

[wherein $R^1$ and $R^2$ are as described above].

$$CO(OR)_2 \qquad (3)$$

[wherein R is as described above].

It is preferable to conduct the reaction by refluxing under heat as a reaction temperature in the presence of inorganic base such as potassium t-butoxide or potassium hydride, preferably sodium hydride, using solvent amount of the compounds of general formula (3).

In the synthetic route 2, compounds represented by a general formula (17)

(17)

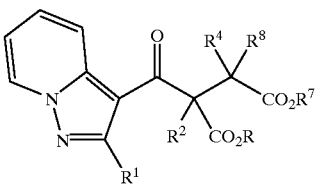

[wherein R, $R^1$, $R^2$, $R^4$, $R^7$ and $R^8$ are as described above], can be prepared by reacting compounds represented by the general formula (16) with compounds represented by the general formula (4)

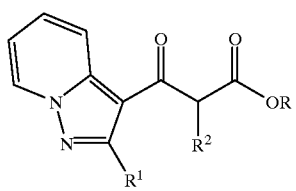

(16)

[wherein R, $R^1$ and $R^2$ are as described above].

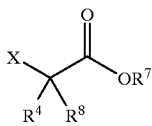

(4)

[wherein X, $R^4$, $R^7$ and $R^8$ are as described above].

It is preferable to conduct the reaction at 0° C. to solvent-refluxing temperature, though the reaction temperature is not restricted particularly, in the presence of inorganic base such as potassium carbonate, potassium t-butoxide or potassium hydride, preferably sodium hydride, using tetrahydrofuran, 1,4-dioxane or 1,2-dimethoxyethane, preferably dimethylformamide as a reaction solvent.

In the synthetic route 2, compounds represented by a general formula (6a)

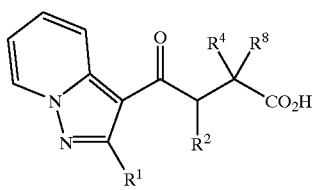

(6a)

[wherein $R^1$, $R^2$, $R^4$ and $R^8$ are as described above], can be prepared by hydrolyzing and decarboxylating the compounds represented by the general formula (17) aforementioned.

In the case of acid catalyst, it is preferable to conduct the hydrolysis and decarboxylation by heating to 80 to 120° C., using hydrochloric acid or hydrobromic acid. Moreover, in the case of alkali catalyst, it is preferable to conduct at room temperature in an alcoholic solvent such as methanol or ethanol or in a solvent such as tetrahydrofuran or dimethylformamide, using aqueous solution of sodium hydroxide or aqueous solution of potassium hydroxide.

In the synthetic route 3, compounds represented by a general formula (9)

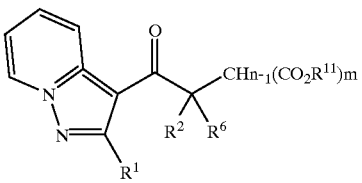

(9)

[wherein $R^1$, $R^2$ and $R^6$ are as described above, $R^{11}$ denotes a lower alkyl group with carbon atoms of 1 to 3, and (n, m) denotes a combination of integers of (1, 3) or (2, 2)], can be prepared by reacting compounds represented by a general formula (7) with compounds represented by a general formula (8).

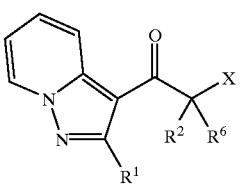

(7)

[wherein X, $R^1$, $R^2$ and $r^6$ are as described above].

$$CH_n(CO_2R^{11})_m \quad (8)$$

[wherein combination of (n, m) and $R^{11}$ are as described above].

It is preferable to conduct the reaction at 0° C. to solvent-refluxing temperature, though the reaction temperature is not restricted particularly, in the presence of inorganic base such as potassium carbonate, potassium t-butoxide or potassium hydride, preferably sodium hydride, using tetrahydrofuran, 1,4-dioxane or 1,2-dimethoxyethane, preferably dimethylformamide as a reaction solvent.

In the synthetic route 3, compounds represented by a general formula (6b)

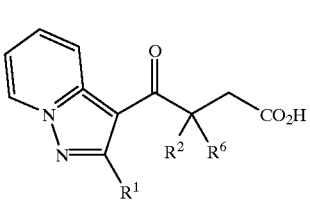

(6b)

[wherein $R^1$, $R^2$ and $R^6$ are as described above], can be prepared by hydrolyzing and decarboxylating the compounds represented by the general formula (9) aforementioned.

In the case of acid catalyst, it is preferable to conduct the hydrolysis and decarboxylation by heating to 80to 120° C., using hydrochloric acid or hydrobromic acid. Moreover, in the case of alkali catalyst, it is preferable to conduct at room temperature in an alcoholic solvent such as methanol or ethanol or in a solvent such as tetrahydrofuran or dimethylformamide, using aqueous solution of sodium hydroxide or aqueous solution of potassium hydroxide.

Best embodiment to put the invention into practice

In following, the invention will be illustrated based on concrete examples, but the invention is not confined to these examples. Moreover, when the compounds of the invention have asymmetric carbons at 4-position and 5-position of dihydropyridazinone ring, there exist optical isomers, which are all included in the invention.

EXAMPLE 1

Methyl 2-methyl-3-(2-methylpyrazolo[1,5-a]pyridine-3-yl)-3-oxopropionate

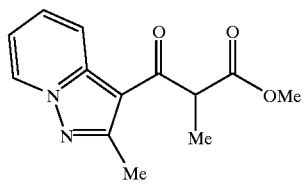

2-Methyl-3-propionylpyrazolo[1,5-a]pyridine (5.28 g) was dissolved into dimethyl carbonate (100 ml), and, after adding sodium hydride (3.37 g), the mixture was refluxed for 8 hours under heat. Under cooling in water bath, acetic acid was added, then, following dilution with water, the mixture was extracted with methylene chloride. After the organic layer was dried over anhydrous sodium sulfate, solvent was distilled off under reduced pressure and the residue was purified by means of silica gel column chromatography (developing solvent, ethyl acetate:n-hexane= 1:3~1:1) to obtain aimed product (5.13 g) as a yellow oily product.

EXAMPLES 2 THROUGH 9

Similarly to Example 1, following compounds were obtained (Table 1).

TABLE 1

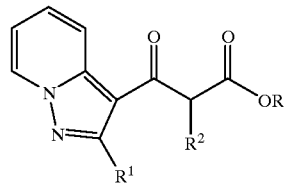

| Example | $R^1$ | $R^2$ | R | Yield (%) | Property |
|---|---|---|---|---|---|
| 2 | Me | Et | Me | 91 | Pale yellow oily product |
| 3 | Et | Me | Me | 93 | Pale yellow oily product |
| 4 | Pr | Me | Me | 54 | Yellow oily product |
| 5 | i-Pr | H | Me | 94 | Pale yellow oily product |
| 6 | i-Pr | Me | Me | 91 | Brown oily product |
| 7 | i-Pr | Et | Me | 87 | Yellow oily product |
| 8 | cyclo-Pr | Me | Me | 46 | Brown oily product |

EXAMPLE 9

Ethyl 4-(2-methylpyrazolo[1,5-a]pyridine-3-yl)-3-methoxycarbonyl-3-methyl-4-oxobutyrate

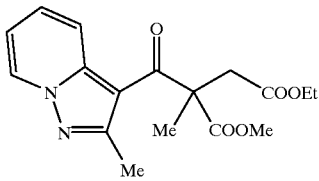

The compound (5.13 g) of Example 1 was dissolved into DMF (70 ml) and, after adding sodium hydride (1.00 g), the mixture was stirred for 1 hour at room temperature. This was cooled in ice bath and ethyl 2-bromoacetate (2.77 ml) was added. After stirring for 18 hours until the temperature rose to room temperature, saturated aqueous solution of ammonium chloride was added and diluted with water, which was extracted with ether. After the organic layer was washed with water and with saturated brine and dried over anhydrous sodium sulfate, solvent was distilled off under reduced pressure. The residue was purified by means of silica gel column chromatography (developing solvent, ethyl acetate:n-hexane=1:2) to obtain aimed product (4.63 g) as a yellow oily product.

EXAMPLES 10 THROUGH 16

By conducting similarly to Example 9 using the compounds of Examples 2 through 8 as raw materials and using ethyl 2-bromoacetate, methyl 2-bromoacetate or methyl 2-bromopropionate, following compounds where obtained (Table 2).

TABLE 2

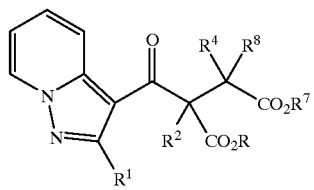

| Example | R¹ | R² | R⁴ | R⁷ | R⁸ | R | Yield (%) | Property |
|---|---|---|---|---|---|---|---|---|
| 10 | Me | Et | H | Me | H | Me | 78 | Yellow oily product |
| 11 | Et | Me | H | Et | H | Me | 70 | Pale yellow oily product |
| 12 | Pr | Me | H | Et | H | Me | 85 | Yellow oily product |
| 13 | i-Pr | H | Me | Me | H | Me | 77 | Pale yellow oily product |
| 14 | i-Pr | Me | H | Et | H | Me | 69 | Pale yellow oily product |
| 15 | i-Pr | Et | H | Et | H | Me | 69 | Yellow oily product |
| 16 | cyclo-Pr | Me | H | Et | H | Me | 37 | Yellow oily product |

EXAMPLE 17

4-(2-Methylpyrazolo[1,5-a]pyridine-3-yl)-3-methyl-4-oxobutyric acid

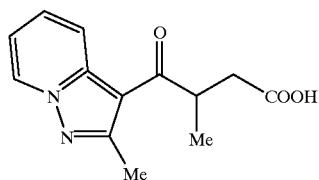

The compound (4.63 g) of Example 9 was dissolved into 47% hydrobromic acid (50 ml) and the solution was refluxed for 1 hour under heat. This was poured into ice water and extracted with methylene chloride. After the organic layer was dried over anhydrous sodium sulfate, solvent was distilled off under reduced pressure. The residue was purified by means of silica gel column chromatography (developing solvent, methylene chloride:ethanol=10:1) to obtain aimed product (2.76 g) as purple powder.

EXAMPLES 18 THROUGH 24

By conducting similarly to Example 17, following compounds were obtained (Table 3).

TABLE 3

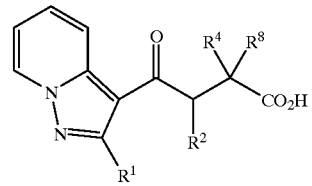

| Example | R¹ | R² | R⁴ | R⁸ | Yield (%) | Property |
|---|---|---|---|---|---|---|
| 18 | Me | Et | H | H | 80 | Brown amorphous material |
| 19 | Et | Me | H | H | 90 | Brown amorphous material |
| 20 | Pr | Me | H | H | 58 | Pale yellow amorphous material |
| 21 | i-Pr | H | Me | H | 99 | Pale pink powder |

TABLE 3-continued

| Example | R¹ | R² | R⁴ | R⁸ | Yield (%) | Property |
|---|---|---|---|---|---|---|
| 22 | i-Pr | Me | H | H | 53 | Colorless powder |
| 23 | i-Pr | Et | H | H | 65 | Pale yellow amorphous material |
| 24 | cyclo-Pr | Me | H | H | 60 | Brown amorphous material |

EXAMPLE 25

Methyl 4-(2-isopropylpyrazolo[1,5-a]pyridine-3-yl)-3-phenyl-4-oxobutyrate

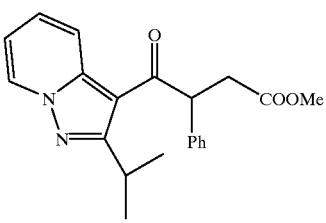

2-Isopropyl-3-phenacylpyrazolo[1,5-a]pyridine (1.90 g) was dissolved into DMF (30 ml), and, after adding sodium hydride (0.35 g), the mixture was stirred for 0.5 hours at room temperature. Methyl 2-bromoacetate (1.36 g) was added, and, after stirring the mixture for 3 hours at room temperature, saturated aqueous solution of ammonium chloride was added and diluted with water, which was extracted with ether. After the organic layer was washed with water and with saturated brine and dried over anhydrous sodium sulfate, solvent was distilled off under reduced pressure. The residue was purified by means of silica gel column chromatography (developing solvent, ethyl acetate:n-hexane=1:3) to obtain aimed product (1.58 g) as a yellow oily product.

EXAMPLE 26

4-(2-Isopropylpyrazolo[1,5-a]pyridine-3-yl)-3-phenyl-4-oxobutyric acid

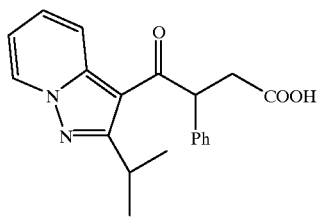

The compound (1.58 g) of Example 25 was dissolved into ethanol (15 ml), and, after adding IN aqueous solution of sodium hydroxide (5 ml), the mixture was stirred for 1 hour at room temperature. water was added to the reaction liquor, then 10% hydrochloric acid was added to make pH 3, which was extracted with methylene chloride. After the organic layer was dried over anhydrous sodium sulfate, solvent was distilled off under reduced pressure to obtain aimed product (1.50 g) as colorless powder.

EXAMPLE 27

Ethyl 2,2-diethoxycarbonyl-4-(2-isopropylpyrazolo-[1,5-a]pyridine-3-yl)-3-methyl-4-oxobutyrate

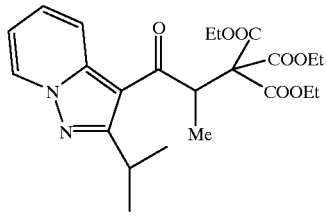

Triethoxycarbonylmethane (1.53 g) was dissolved into DMF (20 ml), and, after adding sodium hydride (0.28 g), the mixture was stirred for 0.5 hours at room temperature. 3-(2-Bromo-propionyl)-2-isopropylpyrazolo[1,5-a]pyridine (1.77 g) was added and the mixture was stirred for 1 hour at room temperature, and then further stirred for 7 hours by heating to 80 to 100° C. Saturated aqueous solution of ammonium chloride was added to the reaction liquor, which was diluted with water, then extracted with ether. After the organic layer was washed with water and with saturated brine and dried over anhydrous sodium sulfate, solvent was distilled off under reduced pressure and the residue was purified by means of silica gel column chromatography (developing solvent, ethyl acetate:n-hexane=1:2) to obtain aimed product (0.67 g) as a yellow oily product.

EXAMPLE 28

Ethyl 2-ethoxycarbonyl-4-(2-isopropylpyrazolo[1,5-a]-pyridine-3-yl)-4-oxobutyrate

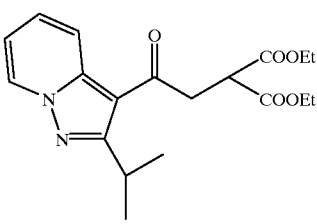

Sodium (0.10 g) was dissolved into ethanol (4 ml) and diethyl malonate (0.71 g) was added at room temperature. After stirring for 20 minutes at 50° C., a solution of 3-(2-bromoacetyl)-2-isopropylpyrazolo[1,5-a]pyridine (1.06 g) in ethanol (6 ml) was added and the mixture was stirred for 75 minutes at 80° C. The reaction liquor was concentrated, and, water and ethyl acetate were added to the residue to separate the organic layer. After the organic layer was washed with water and with saturated brine and dried over anhydrous sodium sulfate, solvent was distilled off and the residue was purified by means of silica gel column chromatography (developing solvent, ethyl acetate, n-hexane=1:3) to obtain aimed product (0.44 g) as pale yellow powder.

EXAMPLE 29

4-(2-Isopropylpyrazolo[1,5-a]pyridine-3-yl)-3-methyl-4-oxobutyric acid

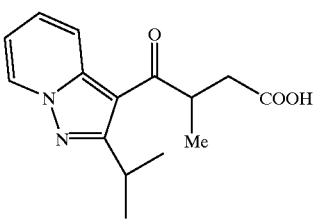

By conducting similarly to Example 17, using the compound (0.67 g) of Example 27, same compound (0.31 g) as that of Example 21 was obtained as pale yellow amorphous material.

EXAMPLE 30

4-(2-Isopropylpyrazolo[1,5-a]pyridine-3-yl)-4-oxobutyric acid

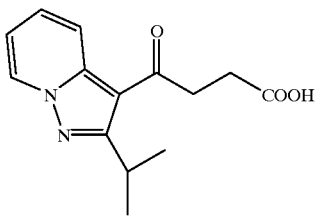

By conducting similarly to Example 17, using the compound (0.72 g) of Example 28, aimed compound (0.52 g) was obtained as colorless powder.

EXAMPLE 31

6-(2-methylpyrazolo[1,5-a]pyridine-3-yl)-5-methyl-4,5-dihydro-3(2H)-pyridazinone

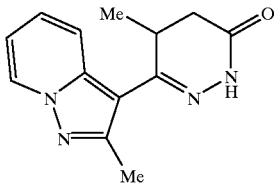

The compound (2.76 g) of Example 17 and hydrazine monohydrate (0.90 g) were dissolved into ethanol (30 ml), and the solution was refluxed for 3 hours under heat. The reaction liquor was submitted to distillation under reduced pressure, and the residue was purified by means of silica gel column chromatography (developing solvent, methylene chloride:ethanol=10:1) to obtain aimed product (2.04 g) as colorless powder. When recrystallizing from isopropyl ether, this gave colorless prismatic crystals.

Melting point:146~147° C.

Elemental analysis (%): As $C_{13}H_{14}N_4O$

|  | C | H | N |
|---|---|---|---|
| Calcd.: | 64.45 | 5.82 | 23.12 |
| Found: | 64.28 | 5.87 | 22.84 |

EXAMPLES 32 THROUGH 40

By conducting similarly to Example 31, following compounds were obtained (Table 4).

TABLE 4

| Example | $R^1$ | $R^2$ | $R^4$ | $R^6$ | $R^8$ | Yield (%) | M.P. (° C.) (Recryst. solvent) | Elemental analysis calcd./found C, H, N |
|---|---|---|---|---|---|---|---|---|
| 32 | Me | Et | H | H | H | 80 | 138~140 i-Pr$_2$O | $C_{14}H_{16}N_4O$ 65.61 6.29 21.86 65.70 6.31 21.72 |
| 33 | Et | Me | H | H | H | 79 | 131~132 i-Pr$_2$O | $C_{14}H_{16}N_4O$ 65.61 6.29 21.86 65.74 6.22 21.85 |
| 34 | Pr | Me | H | H | H | 66 | 141~142 i-Pr$_2$O | $C_{15}H_{18}N_4O$ 66.65 6.71 20.73 66.43 6.64 20.50 |
| 35 | i-Pr | H | H | H | H | 86 | 213.5~215.5 EtOH | $C_{14}H_{16}N_4O$ 65.61 6.29 21.86 65.33 6.31 21.70 |
| 36 | i-Pr | Me | H | H | H | 50 | 119~122 i-Pr$_2$O | $C_{15}H_{18}N_4O$ 66.65 6.71 20.73 66.54 6.73 20.67 |
| 37 | i-Pr | Et | H | H | H | 77 | 147 i-Pr$_2$O | $C_{16}H_{20}N_4O$ 67.58 7.09 19.70 67.47 7.05 19.62 |

TABLE 4-continued

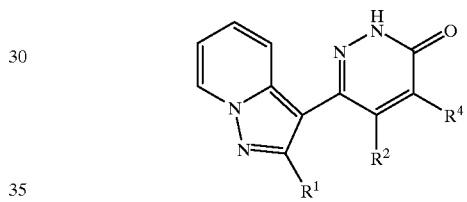

| Example | $R^1$ | $R^2$ | $R^4$ | $R^6$ | $R^8$ | Yield (%) | M.P. (° C.) (Recryst. solvent) | Elemental analysis calcd./found C, H, N |
|---|---|---|---|---|---|---|---|---|
| 38 | i-Pr | Ph | H | H | H | 55 | 192~193 i-Pr$_2$O | $C_{20}H_{20}N_4O$ 71.49 6.12 16.67 71.81 6.25 16.27 but 1/5H$_2$O adduct |
| 39 | i-Pr | H | Me | H | H | 86 | 207~208 EtOH | $C_{15}H_{18}N_4O$ 66.65 6.71 20.73 66.65 6.58 20.74 |
| 40 | cyclo-Pr | Me | H | H | H | 79 | 134 i-Pr$_2$O | $C_{15}H_{16}N_4O$ 67.15 6.01 20.88 67.31 6.07 20.85 |

EXAMPLE 41

6-(2-Ethylpyrazolo[1,5-a]pyridine-3-yl)-5-methyl-3(2H)-pyridazinone

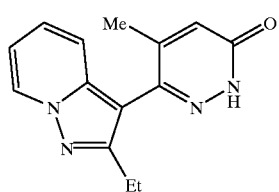

The compound (1.00 g) of Example 36 was dissolved into acetic acid (30 ml), and, after adding bromine (0.22 ml) at 65° C. under stirring, the mixture was stirred for 0.5 hours. The reaction liquor was poured into water, which was extracted with methylene chloride. After the organic layer was washed with water and with saturated aqueous solution of sodium hydrogencarbonate and dried over anhydrous sodium sulfate, solvent was distilled off and the residue was purified by means of silica gel column chromatography (developing solvent, methylene chloride:ethanol=15:1) to obtain aimed product 0.69 g) as pale purple powder. When recrystallizing from ethyl acetate, this gave pale purple prismatic crystals.

Melting point: 216~217° C.

Elemental analysis (%): As $C_{14}H_{14}N_4O$

|  | C | H | N |
|---|---|---|---|
| Calcd.: | 66.13 | 5.55 | 22.03 |
| Found: | 65.96 | 5.49 | 21.90 |

EXAMPLES 42 AND 43

By conducting similarly to Example 41, following compounds were obtained (Table 5).

TABLE 5

| Example | $R^1$ | $R^2$ | $R^4$ | Yield (%) | M.P. (° C.) (Recryst. solvent) | Elemental analysis calcd./found |
|---|---|---|---|---|---|---|
| 42 | i-Pr | H | Me | 71 | 216~217 AcOEt | $C_{15}H_{16}N_4O$ 67.15 6.01 20.88 66.95 5.97 20.82 |
| 43 | i-Pr | H | H | 73 | 225 AcOEt | $C_{14}H_{14}N_4O$ 65.66 5.59 21.88 65.43 5.56 21.64 but 1/10H$_2$O adduct |

EXAMPLE 44

(−)-6-(2-Isopropylpyrazolo [1,5-a]pyridine-3-yl)-5-methyl-4,5-dihydro-3(2H)-pyridazinone and (+)-6-(2-isopropylpyrazolo[1,5-a]pyridine-3-yl)-5-methyl-4,5-dihydro-3(2H)-pyridazinone The compound (1.31 g) of Example 36 was dissolved into 65 ml of mixed liquor of ethanol and hexane (1:4), and this solution was separated automatically by means of HPLC (optical resolution column: Chiralcell OD from Daicel Chemical Industries, Ltd., mobile layer hexane:isopropanol=9:1, injection 1 ml, flow rate 24 ml/min, detecting wavelength 293 nm). Compounds of each fraction obtained were recrystallized from diisopropyl ether to obtain 530 mg of (−) form from eluted fractions of front part and 560 mg of (+) form from eluted fractions of back part as colorless powder, respectively.

(−) Form Melting point 164~165° C., Angle of rotation $[\alpha]_D^{34}$ −179 (C=0.24, CHCl$_3$)

Elemental analysis (%): As $C_{15}H_{18}N_4O$

|         | C     | H    | N     |
|---------|-------|------|-------|
| Calcd.: | 66.66 | 6.71 | 20.73 |
| Found:  | 66.50 | 6.64 | 20.67 |

(+) Form Melting point 164~165° C., Angle of rotation $[\alpha]_D^{34}$ +179 (C=0.24, CHCl$_3$)

Elemental analysis (%): As $C_{15}H_{18}N_4O$

|         | C     | H    | N     |
|---------|-------|------|-------|
| Calcd.: | 66.66 | 6.71 | 20.73 |
| Found:  | 66.26 | 6.75 | 20.48 |

EXPERIMENTAL EXAMPLE

Measurement of phosphodiesterase-inhibiting activity

Phosphodiestorase-containing fractions were extracted from respiratory tract and heart of guinea pig according to the method of Nicholson et al (Br. J. Pharmacol., 97, 889–897 (1989)), and used as enzyme solutions. The measurement of phosphodiesterase-inhibiting activity was performed by quantitatively determining (Linden et al, J. Immunol. Methods., 151, 209–216 (1992)) the cyclic AMP (cAMP) or cyclic GMP (cGMP) that remains as a result of enzymic reaction (Thompson et al, Biochemistry, 10, 311–316 (1971)) through enzyme immunoassay (EIA).

1) Enzymic reaction

This was performed according to the method of Thompson et al. The enzyme solution was placed in a test tube, and 1 μM of cAMP or cGMP was added as a substrate. After reacting for 60 minutes at 30° C., the test tube was dipped for 2 minutes into boiling bath to inactivate phosphodiesterase, thus stopping the reaction. The testing compound was added to the test tube simultaneously with substrate.

2) Quantitative determination through EIA cAMP or cGMP that remained without undergoing decomposition by enzyme solution was quantitatively determined, using EIA kit (from Amasham Co., England) for quantitative determination of CAMP or quantitative determination of cGMP to determine the amount of testing material necessary to inhibit the enzymic reaction by 50% as $IC_{50}$ the results of which are shown in Table 6.

TABLE 6

|            | $IC_{50}$ (μg/ml) | | | | | | |
|------------|-------|---|---|---|---|---|---|
|            | Respiratory tract | | | | Heart | | |
|            | II    | III | IV | V   | I   | II  | III |
| Example 36 | >30   | 4   | 5  | 0.1 | >30 | >30 | 5   |

Utilizability in the industry

The inventive compounds express selective inhibiting effect on phosphodiesterase originating from respiratory tract, in particular, phosphodiesterase V.

What is claimed is:

1. A pyrazolopyridinepyridazinone derivative represented by the formula (1):

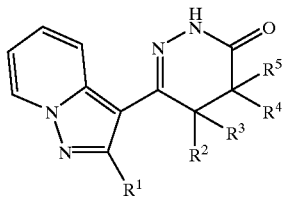

(1)

wherein $R^1$ is a cyclopropyl group, and $R^2$, $R^3$, $R^4$ and $R^5$ are each, independently, a hydrogen atom, a lower alkyl group having 1 to 4 carbon atoms or a phenyl group, or $R^3$ and $R^5$ may combine to form a double bond, or a pharmacologically acceptable salt thereof.

2. The pyrazolopyridinepyridazinone derivative of claim 1, wherein $R^3$ and $R^5$ combine to form a double bond.

3. The pyrazolopyridinepyridazinone derivative of claim 1, wherein $R^2$, $R^3$, $R^4$ and $R^5$ are each, independently, a hydrogen atom, a lower alkyl group having 1 to 4 carbon atoms or a phenyl group.

4. A bronchodilator comprising at least one pyrazolopyridinepyridazinone derivative represented by the formula (1):

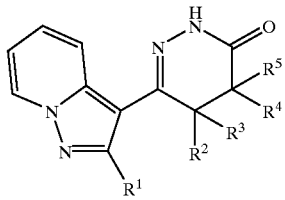

(1)

wherein $R^1$ is a cyclopropyl group, and $R^3$, $R^3$, $R^4$ and $R^5$ each, independently, represent a hydrogen atom, a lower alkyl group having of 1 to 4 carbon atoms or a phenyl group, or $R^3$ and $R^5$ may combine to form a double bond, or a pharmacologically acceptable salt, as an effective ingredient.

5. The bronchodilator of claim 4, wherein $R^3$ and $R^5$ combine to form a double bond.

6. The bronchodilator of claim 4, wherein $R^2$, $R^3$, $R^4$ and $R^5$ are each, independently, a hydrogen atom, a lower alkyl group having 1 to 4 carbon atoms or a phenyl group.

7. A process for preparing a compound represented by the formula (1a):

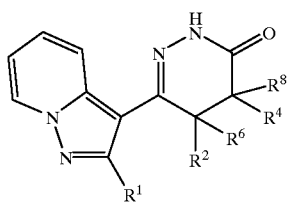

(1a)

wherein
- $R^1$ is a cyclopropyl group, and
- $R^4$, $R^6$ and $R^8$ are each, independently, a hydrogen atom, a lower alkyl group having 1 to 4 carbon atoms or a phenyl group, comprising reacting a compounds represented by the formula (6):

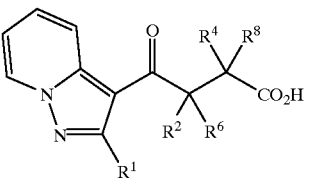

(6)

wherein $R^1$, $R^2$, $R^4$, $R^6$ and $R^8$ are as described above, with hydrazine.

8. A method of inhibiting phosphodiesterase, comprising contacting a phosphodiesterase with the pyrazolopyridinepyridazinone derivative of claim 1.

* * * * *

UNITED STATES PATENT AND TRADEMARK OFFICE
CERTIFICATE OF CORRECTION

PATENT NO.    : 6,265,577 B1
DATED         : July 24, 2001
INVENTOR(S)   : Kouno et al.

It is certified that error appears in the above-identified patent and that said Letters Patent is hereby corrected as shown below:

<u>Title page,</u>
Item [75], the inventors information should read:

-- [75]  Inventors:   Yasushi Kouno, Oyama-shi, Takenobu Ogata, Tokyo; Katsuya Awano, Oyama-shi; Kayoko Matsuzawa, Ageo-shi; Taroh Tooru, Shimotsuga-gun, all of (JP) --

Item [73], the Assignee information should read:

-- [73]  Assignee:    Kyorin Pharmaceutical Co., Ltd., Tokyo (JP) --

Signed and Sealed this

Eighteenth Day of February, 2003

JAMES E. ROGAN
*Director of the United States Patent and Trademark Office*